(12) United States Patent
Besne

(10) Patent No.: US 7,354,956 B2
(45) Date of Patent: Apr. 8, 2008

(54) COMPOSITION CONTAINING A SAPOGENIN AND USE THEREOF

(75) Inventor: Isabelle Besne, Paris (FR)

(73) Assignee: L'Oreal, Paris (FR)

( * ) Notice: Subject to any disclaimer, the term of this patent is extended or adjusted under 35 U.S.C. 154(b) by 597 days.

(21) Appl. No.: 10/393,913

(22) Filed: Mar. 24, 2003

(65) Prior Publication Data

US 2003/0235599 A1 Dec. 25, 2003

Related U.S. Application Data

(60) Provisional application No. 60/374,157, filed on Apr. 22, 2002.

(30) Foreign Application Priority Data

Apr. 12, 2002 (FR) .................................. 02 04611

(51) Int. Cl.
*A01K 47/00* (2006.01)
(52) U.S. Cl. ...................... 514/789; 424/400
(58) Field of Classification Search ...................... None
See application file for complete search history.

(56) References Cited

U.S. PATENT DOCUMENTS

| | | | |
|---|---|---|---|
| 4,267,106 A | 5/1981 | Marx et al. | |
| 4,569,839 A | 2/1986 | Grollier et al. | |
| 5,019,391 A | 5/1991 | Bunte et al. | |
| 5,151,451 A | 9/1992 | Brown et al. | |
| 5,723,149 A | 3/1998 | Bonte et al. | |
| 5,837,224 A | 11/1998 | Voorhees et al. | |
| 5,855,897 A | 1/1999 | Pelle | |
| 5,876,737 A | 3/1999 | Schonrock et al. | |
| 5,895,652 A | 4/1999 | Giampapa | |
| 5,961,981 A | 10/1999 | Gutierrez | |
| 5,989,568 A | 11/1999 | Breton et al. | |
| 6,048,846 A | 4/2000 | Cochran | |
| 6,093,706 A | 7/2000 | Zeligs | |
| 6,110,478 A | 8/2000 | Harang | |
| 6,190,678 B1* | 2/2001 | Hasenoehrl et al. | ........ 424/401 |
| 6,294,157 B1 | 9/2001 | Rubinstenn et al. | |
| 6,331,535 B1 | 12/2001 | Tuloup et al. | |
| 6,623,769 B1 | 9/2003 | Lorant et al. | |
| 2003/0113386 A1 | 6/2003 | Allec et al. | |
| 2003/0124084 A1 | 7/2003 | De Lacharrlere et al. | |
| 2004/0005370 A1 | 1/2004 | Breton | |

FOREIGN PATENT DOCUMENTS

| | | |
|---|---|---|
| AU | 737376 | 11/1998 |
| EP | 0 908 183 | 4/1999 |
| FR | 2 813 194 | * 8/2000 |
| FR | 2 811 568 | 1/2002 |
| JP | 10029924 | 2/1998 |
| WO | WO 97/03676 | 2/1997 |
| WO | WO 98/36742 | 8/1998 |
| WO | WO 99/43329 | 9/1999 |

OTHER PUBLICATIONS

Kyu Suk Lee, et al.: "Effects of dehydroepiandrosterone on collagen and collagenase gene expression by skin fibroblasts in culture", Journal of Dermotological Science, vol. 23, pp. 103-110 (2000).
Soap Perfumery and Cosmetics (May 1999, vol. 72, No. 5, pp. 63) (Abstract Only).

* cited by examiner

*Primary Examiner*—Michael P. Woodward
*Assistant Examiner*—Eric E. Silverman
(74) *Attorney, Agent, or Firm*—Oblon, Spivak, McClelland, Maier & Neustadt, P.C.

(57) ABSTRACT

The present invention relates to a composition containing a sapogenin, and/or a sapogenin ester, and to the use of a sapogenin and/or a sapogenin ester to manufacture a composition that is suitable for topical application to the skin, and in a method wherein sapogenin and/or a sapogenin ester are used as agents for the of smoothing out wrinkles and fine lines, in particular expression wrinkles and fine lines. The sapogenin may be used/provided in the form of a natural extract containing it. A preferred sapogenin is diosgenin.

19 Claims, No Drawings

COMPOSITION CONTAINING A SAPOGENIN AND USE THEREOF

REFERENCE TO PRIOR APPLICATIONS

This application claims priority to U.S. provisional application 60/374,157 filed Apr. 22, 2002, and to French patent application 0204611, filed Apr. 12, 2002, both of which are incorporated herein by reference.

FIELD OF THE INVENTION

The present invention relates to a composition comprising a sapogenin, and/or a sapogenin ester, and to the use of a sapogenin and/or a sapogenin ester to manufacture a composition that is suitable for topical application to the skin, and in a method wherein sapogenin and/or a sapogenin ester are used as agents for the smoothing out wrinkles and fine lines, in particular expression wrinkles and fine lines. The sapogenin may be used/provided in the form of a natural extract containing it. A preferred sapogenin is diosgenin. Diosgenin may be found in certain extracts of plants of the *Dioscorea* genus, in particular in certain extracts of wild yam.

BACKGROUND OF THE INVENTION

Women, and even men, currently have a tendency to wish to look youthful for as long as possible and consequently seek to fade out the age marks on the skin, which are reflected in particular by wrinkles and fine lines. In this respect, the media and the fashion world report about products intended to keep the skin radiant and wrinkle-free for as long as possible, which are signs of youthful skin, and all the more so since the physical appearance acts on the psyche and/or on the morale.

Hitherto, wrinkles and fine lines were treated using cosmetic products containing active agents acting on the skin, for example by moisturizing it or by improving its cell renewal or alternatively by promoting the synthesis of collagen, of which skin tissue is composed.

Although these treatments make it possible to act on the wrinkles and fine lines caused by chronological or intrinsic ageing, and also on those caused by photoageing, they have no effect on expression wrinkles and fine lines.

Hitherto, the only means commonly used for acting on expression wrinkles is botulinum toxin, which is especially injected into the wrinkles of the glabella, i.e. the wrinkles between the eyebrows (see J. D. Carruters et al., *J. Dermatol. Surg. Oncol.*, 1992, 18, pp. 17-21).

Various compounds have been proposed that are capable of affording a muscle-relaxant effect when they are applied topically to the skin, thus making it possible to act on expression wrinkles via another route. Among these compounds that may especially be mentioned are antagonists of the receptors associated with the calcium channels (FR-2 793 681), and in particular manganese and its salts (FR-2 809 005) and alverine (FR-2 798 590); and agonists of the receptors associated with the chlorine channels, including glycine (EP-0 704 210) and certain extracts of Iris pallida (FR-2 746 641).

However, there is still a need for compounds of natural origin that are effective in smoothing out or fading out expression wrinkles and fine lines.

DETAILED DESCRIPTION OF THE PREFERRED EMBODIMENTS

The inventors have now discovered, surprisingly, that sapogenins can satisfy the above need. It is believed that these compounds act on the contractile muscle component of the wrinkles present in the skin. Regardless, the invention provides an effective means for smoothing out wrinkles and fine lines, in particular expression wrinkles and fine lines.

Sapogenins are compounds resulting from the acidic hydrolysis (generally in the presence of hydrochloric acid or sulphuric acid in boiling aqueous medium) or enzymatic hydrolysis (generally for about 5 days at about 37° C.), usually followed by an extraction with an apolar solvent, of saponosides, which are functionalized heterosides of very high molecular weight, present in tubers of certain plants. Sources of saponosides include: plants of the dioscoreacea family, for instance *Dioscorea composita, Dioscorea deltoides, Dioscorea floribunda, Dioscorea sylvatica, Dioscorea spiculiflora* and *Dioscorea villosa*, which are rich in dioscin; plants of the Agave family and plants of the Liliacea family, including yucca.

Among the sapogenins that may be obtained from the abovementioned plants, diosgenin has already been described as an antiinflammatory agent (Yamada et al., *Am. J. Physiol.*, 273:G355-G364, 1997), as a slimming active agent by means of its action on adipocytes (WO 00/30603) and as an antimicrobial agent that may be used in the treatment of various pathologies with an infectious component, including acne and seborrhoeic dermatitis (DE-198 41 795).

In addition, extracts of *Dioscorea tokoro*, which contain dioscin, have moreover been described as being effective in moisturizing the skin and thus softening it. Thus, document JP-10 194 947 discloses an extract of *Dioscorea tokoro* prepared by extraction with water, alcohol or acetone at a temperature of between 0 and 50° C., preferably of 0° C. This extract is described as being useful for improving the suppleness and moisturization of the skin on account of the glycoproteins it contains, especially with a view to preventing the formation of wrinkles. A reduction in the depth of the crow's-foot wrinkles is also observed.

For its part, document JP-2000 143 488 discloses a composition for preventing and improving dryness of the skin, comprising an extract of a plant chosen from a long list, including *Dioscorea tokoro maquino* and *Dioscorea gracillima miq.*, which are sources of saponosides. In this case also, the extraction process involves simply immersing the plant in a solvent at room temperature, followed by filtration and drying steps.

Thus, extraction processes described in these documents do not make it possible to obtain compositions containing sapogenins (including diosgenin), since they do not comprise an acidic or enzymatic hydrolysis step. The compositions described therefore contain only saponosides (including dioscin).

Moreover, patent application FR-00/16074 (unpublished) discloses the use of sapogenins as anti-collagenase agents, in cosmetic compositions intended especially for preventing the formation of wrinkles.

It is not suggested that these compositions can have an effect of smoothing out the existing wrinkles and fine lines, in particular expression wrinkles and fine lines.

One embodiment of the present invention is thus the use of a sapogenin, of a natural extract containing it, and/or of a sapogenin ester, to manufacture a composition that is suitable for topical application to the skin, for smoothing out wrinkles and fine lines.

Another embodiment of the invention is the use of a sapogenin, of a natural extract containing it, and/or of a sapogenin ester, in a composition that is suitable for topical application to the skin, as an agent for smoothing out wrinkles and fine lines.

Another embodiment of the invention is the use of a sapogenin, of a natural extract containing it, and/or of a sapogenin ester, preferably in a composition that is suitable for topical application to the skin, as an agent for smoothing out wrinkles and fine lines, particularly expression wrinkles, and more particularly existing wrinkles and fine lines, in particular expression wrinkles and fine lines. Since the inventors have demonstrated a muscle-relaxant effect of sapogenins and esters, the wrinkles and fine lines concerned are more particularly expression wrinkles.

The sapogenin, natural extract containing it, and/or sapogenin ester, and composition contining same, is thus advantageously intended to be applied to areas of the face or forehead marked by expression wrinkles and fine lines, and/or to individuals with expression wrinkles and fine lines.

The wrinkles and fine lines concerned are preferably those lying radially around the mouth and/or the eyes, in particular crow's-foot wrinkles, and/or lying on the forehead, in particular the "lion" wrinkle, located in the glabella, in the space between the eyebrows, and/or lying horizontally on the forehead.

Sapogenins that may be used according to the invention include diosgenin, hecogenin, smilagenin, sarsapogenin, tigogenin, yamogenin and yuccagenin.

However, in a preferred embodiment, the present invention relates more particularly to diosgenin. Diosgenin is especially available from the company Sabinsa under the trade name Diosgenin®.

The expression "natural extracts" means any plant extract containing one or more sapogenins, after a treatment intended to hydrolyse the saponosides, such as an extract of a Dioscoreacea plant, which contains diosgenin, or an extract of an Agave leaf containing hecogenin and tigogenin, or alternatively an extract of a Liliacea plant, in particular of the genus Smilax or Yucca, containing smilagenin and sarsapogenin, such as an extract of sarsaparilla root.

Thus, the diosgenin may be extracted from the tubers of certain Dioscoreacea plants, as indicated above, by means of a process successively comprising: hot hydrolysis of the heterosides in mineral acid medium (optionally after fermentation and drying of the tubers); and filtration of the insoluble fraction, which is then neutralized, washed and treated with an apolar solvent. However, other extraction processes may be used.

The varieties of Dioscoreacea plants containing dioscin, a diosgenin precursor, are listed in the publication by Franklin W. Martin, The Species of Dioscorea Containing Sapogenin, *Econ. Bot.*, Vol. 23, 373-384 (1969), to which reference may be made.

Among these, mention may be made of the species *Dioscorea composita, Dioscorea deltoides, Dioscorea floribunda, Dioscorea sylvatica, Dioscorea spiculiflora, Dioscorea opposita, Dioscorea mexicana* and *Dioscorea villosa*. The extract used according to the invention is preferably prepared from plant material obtained from the species *Dioscorea villosa* and *Dioscorea opposita*. Such an extract is especially available from the company Active Organics under the trade names Actigen Y® and Actiphyte Mexican Wild Yam®. As a variant, it may be obtained from the company Osst under the trade name Wild Yam P.E.® or from the company Alban Müller under the trade name Extrait sec igname sauvage®. An especially useful sapogenin ester is hecogenin acetate.

The amount of sapogenin and/or ester that may be used according to the invention depends on the desired effect and may thus vary within a wide range, this determination being within the skill of the ordinary artisan in view of this disclosure.

To give an order of magnitude, the total sapogenin and/or ester thereof may be used for example in an amount representing from 0.001% to 5% of the total weight of the composition, and preferably in an amount representing from 0.01% to 1.5% of the total weight of the composition.

The composition according to the invention is suitable for topical application to the skin and thus contains a physiologically acceptable medium, i.e. a medium that is compatible with the skin and optionally its integuments (eyelashes, nails and hair) and/or mucous membranes.

This composition may be in any form, and preferably is in a form normally used in cosmetics, and it may especially be in the form of an optionally gelled aqueous solution, a dispersion of the lotion type, optionally a two-phase lotion, an emulsion obtained by dispersing a fatty phase in an aqueous phase (O/W emulsion) or conversely (W/O emulsion), or a triple emulsion (W/O/W or O/W/O emulsion) or a vesicular dispersion of ionic and/or nonionic type. These compositions can be prepared according to the usual methods. A composition in the form of an oil-in-water emulsion is preferably used according to this invention.

This composition may be more or less fluid and may have the appearance of a white or coloured cream, an ointment, a milk, a lotion, a serum, a paste or a mousse. It may optionally be applied in the form of an aerosol. It may also be in solid form, in particular in the form of a stick. It may be used as a care product, and/or as a makeup product for the skin.

The compositions according to the invention may also contain adjuvants that are common in cosmetics, such as hydrophilic or lipophilic gelling agents, hydrophilic or lipophilic active agents, preserving agents, antioxidants, solvents, fragrances, fillers, screening agents, pigments, odour absorbers and dyestuffs. The amounts of these various adjuvants are those conventionally used in the field under consideration, and may be, for example, from 0.01% to 20% relative to the total weight of the composition. Depending on their nature, these adjuvants may be introduced into the fatty phase, into the aqueous phase, or into lipid vesicles. In any case, these adjuvants, and also the proportions thereof, are preferably chosen so as not to harm the desired properties of the sapogenins, sapogenin esters, or of the natural extracts according to the invention.

When the composition used according to the invention is an emulsion, the proportion of the fatty phase may preferably range from 5% to 80% by weight and more preferably from 5% to 50% by weight relative to the total weight of the composition. The oils, emulsifiers and any co-emulsifiers used in the composition in emulsion form may be chosen from those conventionally used in the field under consideration. The emulsifier and any co-emulsifier are preferably present in the composition in a proportion ranging from 0.3% to 30% by weight and more preferably from 0.5% to 20% by weight relative to the total weight of the composition.

Useful oils which may be used in the invention include mineral oils (liquid petroleum jelly), oils of plant origin (avocado oil or soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax or ozokerite) may also be used as fatty substances.

Useful emulsifiers and co-emulsifiers that may be used in the invention include fatty acid esters of polyethylene glycol such as PEG-100 stearate, and fatty acid esters of glycerol such as glyceryl stearate.

Useful hydrophilic gelling agents include carboxyvinyl polymers (carbomer), acrylic copolymers such as acrylate/alkylacrylate copolymers, polyacrylamides, polysaccharides, natural gums and clays, and lipophilic gelling agents that may be mentioned include modified clays, for instance bentones, metal salts of fatty acids, hydrophobic silica and polyethylenes.

As active agents, it will be advantageous to introduce into the composition used according to the invention at least one compound chosen from: desquamating agents; moisturizers; depigmenting or propigmenting agents; antiglycation agents; NO-synthase inhibitors; agents for stimulating the synthesis of dermal or epidermal macromolecules and/or for preventing their degradation; agents for stimulating the proliferation of fibroblasts and/or keratinocytes or for stimulating the differentiation of keratinocytes; muscle relaxants; tensioning agents; antipollution agents and/or free-radical scavengers; agents acting on the capillary circulation; agents acting on the energy metabolism of cells; and mixtures thereof.

Examples of such additional compounds are given below.

1. Desquamating Agents

The term "desquamating agent" means any compound capable of acting:

either directly on the desquamation by promoting exfoliation, such as β-hydroxy acids, in particular salicylic acid and its derivatives (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; extract of Saphora japonica; resveratrol;

or on the enzymes involved in the desquamation or degradation of corneodesmosomes, glycosidases, stratum corneum chymotryptic enzyme (SCCE), or even other proteases (trypsin, chymotrypsin-like). Mention may be made of agents for chelating mineral salts: EDTA; N-acyl-N,N',N'-ethylenediaminetriacetic acid; aminosulphonic compounds and in particular (N-2-hydroxyethylpiperazine-N-2-ethane)sulphonic acid (HEPES); 2-oxothiazolidine-4-carboxylic acid (procysteine); α-amino acid derivatives of the type such as glycine (as described in EP-0 852 949, and sodium methyl glycine diacetate sold by BASF under the trade name Trilon M); honey; sugar derivatives such as O-octanoyl-6-D-maltose and N-acetylglucosamine.

2. Moisturizer

The term "moisturizer" means:

either a compound acting on the barrier function, in order to maintain the moisturization of the stratum corneum, or an occlusive compound. Mention may be made of ceramides, sphingoid-based compounds, lecithins, glycosphingolipids, phospholipids, cholesterol and its derivatives, phytosterols (stigmasterol, β-sitosterol or campesterol), essential fatty acids, 1,2-diacylglycerol, 4-chromanone, pentacyclic triterpenes such as ursolic acid, petroleum jelly and lanolin;

or a compound that directly increases the water content of the stratum corneum, such as threalose and its derivatives, hyaluronic acid and its derivatives, glycerol, pentanediol, sodium pidolate, serine, xylitol, sodium lactate, polyglyceryl acrylate, ectoin and its derivatives, chitosan, oligosaccharides and polysaccharides, cyclic carbonates, N-lauroylpyrrolidonecarboxylic acid and N-α-benzoyl-L-arginine;

or a compound that activates the sebaceous glands, such as DHEA and its derivatives and vitamin D and its derivatives.

3. Depigmenting or Propigmenting Agent

The depigmenting agents that may be incorporated into the composition according to the present invention comprise, for example, the following compounds: kojic acid; ellagic acid; arbutin and its derivatives such as those described in patent applications EP-895 779 and EP-524 109; hydroquinone; aminophenol derivatives such as those described in patent applications WO 99/10318 and WO 99/32077, and in particular N-cholesteryloxycarbonyl-para-aminophenol and N-ethyloxycarbonyl-para-aminophenol; iminophenol derivatives, in particular those described in patent application WO 99/22707; L-2-oxothiazolidine-4-carboxylic acid or procysteine, and also its salts and esters; ascorbic acid and its derivatives, especially ascorbyl glucoside; and plant extracts, in particular extracts of liquorice, of mulberry and of skullcap, without this list being limiting.

Propigmenting agents that may be mentioned include the extract of burnet (Sanguisorba officinalis) sold by the company Maruzen, and extracts of chrysanthemum (Chrysanthemum morifolium).

4. Anti-glycation Agent

The term "anti-glycation agent" means a compound for preventing and/or reducing the glycation of skin proteins, in particular of dermal proteins such as collagen.

Examples of anti-glycation agents are plant extracts of the Ericacea family, such as an extract of blueberry (Vaccinium angustifolium); ergothioneine and its derivatives; and hydroxystilbenes and their derivatives, such as resveratrol and 3,3',5,5'-tetrahydroxystilbene. Resveratrol is particularly preferred for use in this invention.

5. NO-synthase Inhibitor

Examples of NO-synthase inhibitors that are suitable for use in the present invention especially comprise a plant extract of the species Vitis vinifera which is sold especially by the company Euromed under the name Leucocyanidines de raisins extra, or by the company Indena under the name Leucoselect®, or finally by the company Hansen under the name Extrait de marc de raisin; a plant extract of the species Olea europaea which is preferably obtained from olive tree leaves and is sold especially by the company Vinyals in the form of a dry extract, or by the company Biologia & Technologia under the trade name Eurol BT; and a plant extract of the species Gingko biloba which is preferably a dry aqueous extract of this plant sold by the company Beaufour under the trade name Gingko biloba extrait standard.

6. Agent for Stimulating the Synthesis of Dermal or Epidermal Macromolecules and/or for Preventing their Degradation Among the active agents for stimulating dermal macromolecules or for preventing their degradation, mention may be made of those that act:

either on collagen synthesis, such as extracts of Centella asiatica; asiaticosides and derivatives; ascorbic acid or vitamin C and its derivatives; synthetic peptides such as lamin, biopeptide CL or the palmitoyloligopeptide sold by the company Sederma; peptides extracted from plants, such as the soybean hydrolysate sold by the company Coletica under the trade name Phytokine®; and plant hormones such as auxins;

or on elastin synthesis, such as the extract of *Saccharomyces cerivisiae* sold by the company LSN under the trade name Cytovitin®; and the extract of the alga *Macrocystis pyrifera* sold by the company SECMA under the trade name Kelpadelie®;

or on glycosaminoglycan synthesis, such as the product of fermentation of milk with *Lactobacillus vulgaris*, sold by the company Brooks under the trade name Biomin yogourth®; the extract of the brown alga *Padina pavonica* sold by the company Alban Müller under the trade name HSP3®; and the extract of *Saccharomyces cerevisiae* available especially from the company Silab under the trade name Firmalift® or from the company LSN under the trade name Cytovitin®;

or on fibronectin synthesis, such as the extract of the zooplankton Salina sold by the company Seporga under the trade name GP4G®; the yeast extract available especially from the company Alban Müller under the trade name Drieline®; and the palmitoyl pentapeptide sold by the company Sederma under the trade name Matrixil®;

or on metalloprotease (MMP) inhibition, such as, more particularly, MMP 1, 2, 3 or 9. Mention may be made of: retinoids and derivatives, oligopeptides and lipopeptides, lipoamino acids, the malt extract sold by the company Coletica under the trade name Collalift®; extracts of blueberry or of rosemary; lycopene; isoflavones, their derivatives or plant extracts containing them, in particular extracts of soybean (sold, for example, by the company Ichimaru Pharcos under the trade name Flavosterone SB®), of red clover, of flax, of kakkon, or of sage;

or on the inhibition of serine proteases such as leukocyte elastase or cathepsin G. Mention may be made of: the peptide extract of Leguminosa seeds (*Pisum sativum*) sold by the company LSN under the trade name Parelastyl®; heparinoids; and pseudodipeptides.

Among the active agents that stimulate epidermal macromolecules, such as fillagrin and keratins, mention may be made especially of the extract of lupin sold by the company Silab under the trade name Structurine®; the extract of beech *Fagus sylvatica* buds sold by the company Gattefosse under the trade name Gatuline®; and the extract of the zooplankton Salina sold by the company Seporga under the trade name GP4G®.

7. Agent for Stimulating the Proliferation of Fibroblasts or Keratinocytes and/or Keratinocyte Differentiation The agents for stimulating the proliferation of fibroblasts that may be used in the composition according to the invention may be chosen, for example, from plant proteins or polypeptides, extracts, especially of soybean (for example an extract of soybean sold by the company LSN under the name Eleseryl SH-VEG 8® or sold by the company Silab under the trade name Raffermine®); and plant hormones such as giberrellins and cytokinins.

The agents for stimulating keratinocyte proliferation that may be used in the composition according to the invention especially comprise retinoids such as retinol and its esters, including retinyl palmitate; phloroglucinol; extracts of nut cakes sold by the company Gattefosse; and extracts of *Solanum tuberosum* sold by the company Sederma.

The agents for stimulating keratinocyte differentiation comprise, for example, minerals such as calcium; the extract of lupin sold by the company Silab under the trade name Photopreventine®; sodium beta-sitosteryl sulphate sold by the company Seporga under the trade name Phytocohesine®; and the extract of corn sold by the company Solabia under the trade name Phytovityl®.

8. Muscle Relaxant

Besides the sapogenin described above, the composition according to the invention may comprise other muscle relaxants, among which mention may be made in particular of alverine and its salts, especially alverine citrate, manganese gluconate and the hexapeptide argireline R sold by the company Lipotec.

9. Tensioning Agent

The term "tensioning agent" means a compound capable of exerting tension on the skin, the effect of which is to temporarily fade out irregularities on the skin's surface, such as wrinkles and fine lines.

Among the tensioning agents that may be used in the composition according to the present invention, mention may be made especially of:

(1) synthetic polymers, such as polyurethane latices or acrylic-silicone latices, in particular those described in patent application EP-1 038 519, such as a propylthio (polymethyl acrylate), propylthio(polymethyl methacrylate) and propylthio(polymethacrylic acid) grafted polydimethylsiloxane, or alternatively a propylthio (polyisobutyl methacrylate) and propylthio (polymethacrylic acid) grafted polydimethylsiloxane. Such grafted silicone polymers are sold especially by the company 3M under the trade names VS 80, VS 70 or LO21.

(2) polymers of natural origin, especially (a) polyholosides, for example (i) in the form of starch derived especially from rice, corn, potato, cassava, pea, *Triticum aestivum* wheat, oat, etc. or (ii) in the form of carrageenans, alginates, agars, gelans, cellulose-based polymers and pectins, advantageously as an aqueous dispersion of gel microparticles, and (b) latices consisting of shellac resin, sandarac gum, dammar resins, elemi gums, copal resins and cellulose-based derivatives, and mixtures thereof, (3) plant proteins and protein hydrolysates, in particular from corn, rye, *Triticum aestivum* wheat, buckwheat, sesame, spelt, pea, bean, lentil, soybean and lupin, (3) mixed silicates, especially phyllosilicates and in particular Laponites, (4) wax microparticles chosen, for example, from carnauba wax, candelilla wax and alfalfa wax, (5) colloidal particles of mineral filler with a number-average diameter of between 0.1 and 100 nm and preferably between 3 and 30 nm, chosen, for example, from: silica, cerium oxide, zirconium oxide, alumina, calcium carbonate, barium sulphate, calcium sulphate, zinc oxide and titanium dioxide.

10. Anti-pollution Agent or Free-radical Scavenger

The term "anti-pollution agent" means any compound capable of trapping ozone, monocyclic or polycyclic aromatic compounds such as benzopyrene and/or heavy metals such as cobalt, mercury, cadmium and/or nickel. The term "free-radical scavenger" means any compound capable of trapping free radicals.

As ozone-trapping agents that may be used in the composition according to the invention, mention may be made in particular of vitamin C and its derivatives including ascorbyl glucoside; phenols and polyphenols, in particular tannins, ellagic acid and tannic acid; epigallocatechin and natural extracts containing it; extracts of olive tree leaf; extracts of tea, in particular of green tea; anthocyans; extracts of rosemary; phenol acids, in particular chlorogenic acid; stilbenes, in particular resveratrol; sulphur-containing amino acid derivatives, in particular S-carboxymethylcysteine; ergothioneine; N-acetylcysteine; chelating agents for instance N,N'-bis(3,4,5-trimethoxybenzyl)ethylenediamine or one of its salts, metal complexes or esters; carotenoids such as crocetin; and various starting materials, for instance the mixture of arginine, histidine ribonucleate, mannitol, adenosine triphosphate, pyridoxine, phenylalanine, tyrosine and hydrolysed RNA, sold by the Laboratoires Sérobiologiques under the trade name CPP LS 2633-12F®, the water-soluble fraction of corn sold by the company Solabia under the trade name Phytovityl®, the mixture of extract of fumitory and of extract of lemon sold under the name Unicotrozon C-49® by the company Induchem, and the mixture of extracts of ginseng, of apple, of peach, of wheat and of barley, sold by the company Provital under the trade name Pronalen Bioprotect®.

As agents for trapping monocyclic or polycyclic aromatic compounds, which may be used in the composition according to the invention, mention may be made in particular of tannins such as ellagic acid; indole derivatives, in particular 3-indolecarbinol; extracts of tea, in particular of green tea, extracts of water hyacinth or *Eichhornia crassipes*; and the water-soluble fraction of corn sold by the company Solabia under the trade name Phytovityl®.

Finally, as heavy-metal-trapping agents that may be used in the composition according to the invention, mention may be made in particular of chelating agents such as EDTA, the pentasodium salt of ethylenediaminetetramethylenephosphonic acid, and N,N'-bis(3,4,5-trimethoxybenzyl)ethylenediamine or one of the salts, metal complexes or esters thereof; phytic acid; chitosan derivatives; extracts of tea, in particular of green tea; tannins such as ellagic acid; sulphur-containing amino acids such as cysteine; extracts of water hyacinth (*Eichhornia crassipes*); and the water-soluble fraction of corn sold by the company Solabia under the trade name Phytovityl®.

The free-radical scavengers that may be used in the composition according to the invention comprise, besides certain anti-pollution agents mentioned above, vitamin E and its derivatives such as tocopheryl acetate; bioflavonoids; coenzyme Q10 or ubiquinone; certain enzymes, for instance catalase, superoxide dismutase, lactoperoxidase, glutathione peroxidase and quinone reductases; glutathione; benzylidenecamphor; benzylcyclanones; substituted napthalenones; pidolates; phytanetriol; gamma-oryzanol; lignans; and melatonin.

11. Agents Acting on the Capillary Circulation

The active agents acting on the capillary circulation (vasoprotective or vasodilating agents) are found especially among flavonoids, ruscogenins, esculosides, escin extracted from common horse chestnut, nicotinates, heperidine methyl chalcone, essential oils of lavender or of rosemary, and extracts of *Ammi Visnaga*.

12. Agents Acting on the Energy Metabolism of Cells

This expression means active agents acting on the energy metabolism of the skin, such as, for example, and in a non-limiting manner, ATP synthesis, and also those involved in the respiratory chain of the cell or in the energy reserves. Mention may be made in this respect of coenzyme Q10 (ubiquinone), cytochrome C, creatine or phosphocreatine.

As mentioned previously, the composition according to the invention may also contain UVA and/or UVB screening agents, in the form of organic or mineral compounds, the latter optionally being coated to make them hydrophobic.

The organic screening agents may be chosen especially from: anthranilates, in particular menthyl anthranilate; benzophenones, in particular benzophenone-1, benzophenone-3, benzophenone-5, benzophenone-6, benzophenone-8, benzophenone-9, benzophenone-12 and, preferably, benzophenone-2 (oxybenzone) or benzophenone-4 (Uvinul MS40 available from BASF); benzylidenecamphors, in particular 3-benzylidenecamphor, benzylidenecamphorsulphonic acid, camphor benzalkonium methosulphate, polyacrylamidomethylbenzylidenecamphor, terephthalylidenedicamphorsulphonic acid and, preferably, 4-methylbenzylidenecamphor (Eusolex 6300 available from Merck); benzimidazoles, in particular benzimidazilate (Neo Heliopan AP available from Haarmann & Reimer), or phenylbenzimidazolesulphonic acid (Eusolex 232 available from Merck); benzotriazoles, in particular drometrizole trisiloxane, or methylenebis-benzotriazolyltetramethylbutylphenol (Tinosorb M available from Ciba); cinnamates, in particular cinoxate, DEA methoxycinnamate, diisopropyl methylcinnamate, glyceryl ethylhexanoate dimethoxycinnamate, isopropyl methoxycinnamate, isoamyl cinnamate and, preferably, ethocrylene (Uvinul N35 available from BASF), octyl methoxycinnamate (Parsol MCX available from Hoffmann LaRoche), or octocrylene (Uvinul 539 available from BASF); dibenzoylmethanes, in particular butylmethoxydibenzoylmethane (Parsol 1789); imidazolines, in particular ethylhexyl dimethoxybenzylidene dioxoimidazoline; PABAs, in particular ethyl dihydroxypropyl PABA, ethylhexyldimethyl PABA, glyceryl PABA, PABA, PEG-25 PABA and, preferably, diethylhexylbutamidotriazone (Uvasorb HEB available from 3V Sigma), ethylhexyltriazone (Uvinul T150 available from BASF) or ethyl PABA (benzocaine); salicylates, in particular dipropylene glycol salicylate, ethylhexyl salicylate, homosalate or TEA salicylate; triazines, in particular anisotriazine (Tinosorb S available from Ciba); drometrizole trisiloxane.

The mineral screening agents preferably consist of zinc oxide and/or titanium dioxide, preferably of nanometric size, optionally coated with alumina and/or stearic acid.

The invention will now be illustrated by the non-limiting examples that follow. In these examples, the amounts are indicated as percentages by weight.

EXAMPLES

Example 1

Demonstration of the Muscle-relaxant Effect of Sapogenins

Hecogenin acetate and diosgenin, sold by Sigma, were tested on a model of nerve/muscle (motor plate) junction obtained in a phrenic nerve/diaphragm preparation isolated from rat (striated muscle) (Pollard B. J. et al, *Br. J. Anaesth.*, 1988, 61, 419-424).

The phrenic nerve and the diaphragm are carefully isolated and placed in a 50 ml tank filled with survival liquid (Krebs-Henseleit liquid) maintained at a temperature of 37° C. and oxygenated with an oxygen/$CO_2$ mixture (95/5).

The tension variations of the diaphragm are recorded with an initial pre-load of several grams.

After a relaxation period of 30 minutes, the diaphragm is stimulated indirectly via the phrenic nerve.

On each preparation, the effect of the test products was evaluated on the contractions induced by indirect stimulation via stimulation on the phrenic nerve (0.1 to 0.5 volt, 0.3 ms, 0.1 Hz) at increasing and cumulative concentrations from $10^{-10}$ M to $10^{-5}$ M.

The results obtained in the motor plate model with the sapogenins are given in the table below:

| PRODUCT | CONCENTRATION | % INHIBITION OF CONTRACTIONS | IC$_{50}$* |
|---|---|---|---|
| Diosgenin | $10^{-5}$ M | 100% | $10^{-6}$ M |
| Hecogenin acetate | $10^{-5}$ M | 100% | $2.5 \times 10^{-6}$ M |

*Concentration to obtain 50% of the inhibitory effect

For comparative purposes, at a concentration of $10^{-4}$ M, alverine completely inhibits the contractions induced by the indirect stimulations. On the other hand, it has no effect on these contractions at a concentration of $10^{-5}$ M.

Thus, diosgenin and hecogenin acetate are more effective muscle relaxants than alverine and are useful for this purpose in smoothing out expression wrinkles and fine lines.

Example 2

Cosmetic Compositions

These compositions are prepared in a manner that is conventional for those skilled in the art. The amounts given in these examples are indicated as percentages by weight.

A. Cream

| | |
|---|---|
| Mixture of cetearyl alcohol and of cetearyl glucoside | 4% |
| Mixture of glyceryl stearate and of PEG-100 stearate | 1% |
| Cetyl alcohol | 0.5% |
| C$_{12-15}$ alkyl benzoate | 2% |
| Hydrogenated polyisobutene | 5% |
| Petroleum jelly | 2% |
| Plant oils | 3.5% |
| Silicone wax | 2% |
| Volatile silicone | 5% |
| Extract of *Padina pavonica* | 1% |
| Extract of wild yam | 0.7% |
| Isoflavone-rich extract of soybean | 1% |
| PEG-20 | 1% |
| Alcohol | 3% |
| Glycerol | 7% |
| Gelling agents | 1.5% |
| UVA and UVB screening agents | 12.5% |
| Neutralizer | 1.5% |
| Preserving agents | qs |
| Water | qs 100% |

This cream is intended to be applied to the face and the forehead to attenuate expression wrinkles and fine lines.

B. Serum

| | |
|---|---|
| Octyldodecanol | 0.4% |
| Hecogenin acetate | 0.1% |
| Preserving agents | qs |
| Butylene glycol | 1% |
| Sodium hydroxide | 0.7% |
| Glyceryl stearate and PEG-100 stearate | 0.3% |
| PEG-60 hydrogenated castor oil | 1% |
| Ethanol | 5% |
| Disodium EDTA | 0.05% |
| Gelling agents | 2.5% |
| Polysilicone-8 | 1% |
| Sodium hyaluronate | 0.1% |
| Glycerol | 4% |
| Dimethicone and dimethiconol | 3% |
| 5-n-Octanoylsalicylic acid | 0.2% |
| Soybean protein | 1% |
| Extract of the brown alga *Padina pavonica* | 1% |
| Citric acid | 1.2% |
| Water | qs 100% |

This serum is intended to be applied around the mouth to attenuate vertical wrinkles and fine lines.

C. Cream for Around the Eyes

| | |
|---|---|
| Glycerol | 12% |
| Extract of *Dioscorea villosa* root | 0.35% |
| Extract of *Ruscus aculeatus* root | 0.1% |
| Cyclohexasiloxane | 4% |
| Dimethicone and dimethiconol | 0.5% |
| Plant oils | 9% |
| Fatty alcohols | 1.7% |
| Myristyl myristate | 1% |
| PEG-40 stearate and glyceryl stearate | 0.9% |
| Sorbitan tristearate | 0.2% |
| Potassium cetyl phosphate | 0.7% |
| Carbomer | 0.5% |
| Silica | 2% |
| Escin | 0.1% |
| Preserving agents | qs |
| Triethanolamine | 0.5% |
| Disodium EDTA | 0.2% |
| Water | qs 100% |

This cream, used daily around the eyes, makes it possible to fade out the crow's-feet wrinkles and fine lines.

The above written description of the invention provides a manner and process of making and using it such that any person skilled in this art is enabled to make and use the same, this enablement being provided in particular for the subject matter of the appended claims and including the use of a sapogenin, of a natural extract containing it, of a sapogenin ester, or a mixture thereof to manufacture a composition that is suitable for topical application to the skin (for example by a method comprising mixing one or a mixture of two or more of such substances with a physiologically acceptable medium in appropriate amounts), for smoothing out wrinkles and fine lines, and the use of a sapogenin, of a natural extract containing it, of a sapogenin ester, or a mixture thereof in a composition that is suitable for topical application to the skin, as an agent for smoothing out wrinkles and fine lines these uses especially targeted to expression wrinkles, wrinkles and fine lines that lie radially around the mouth and/or the eyes and/or horizontally on the forehead and/or are located in the space between the eyebrows, and areas of the face or the forehead marked by expression wrinkles and fine lines and/or to individuals with expression wrinkles and fine lines.

Preferred embodiments of the invention similarly fully described and enabled are a method, comprising applying a substance selected from the group consisting of a sapogenin, a natural extract comprising a sapogenin, a sapogenin ester, and mixtures thereof to at least one area of the face or the forehead marked by at least one of a wrinkle and a fine line. Preferably, the substance may be a sapogenin selected from the group consisting of diosgenin, hecogenin, smilagenin, sarsapogenin, tigogenin, yamogenin and yuccagenin, a natural extract selected from the group of extracts of rhizomes of *Dioscorea composita*, *Dioscorea deltoides*, *Dioscorea floribunda*, *Dioscorea sylvatica*, *Dioscorea spiculiflora*, *Dioscorea opposita*, *Dioscorea mexicana* and *Dioscorea villosa*, and hecogenin acetate.

In another preferred embodiment both described and enabled herein, the substance is present in a composition suitable for topical application to skin, and the substance is present in an amount of 0.1% to 1.5% of the total weight of the composition. This composition may further comprise at least one compound selected from the group consisting of desquamating agents; moisturizers; depigmenting or propigmenting agents; antiglycation agents; NO-synthase inhibitors; agents for stimulating the synthesis of dermal or epidermal macromolecules and/or for preventing their degradation; agents for stimulating the proliferation of fibroblasts and/or keratinocytes or for stimulating the differentiation of keratinocytes; muscle relaxants; tensioning agents; antipollution agents and/or free-radical scavengers; agents acting on the capillary circulation; agents acting on the energy metabolism of cells; and mixtures thereof. The invention method is particularly useful where the area of the face or the forehead is marked by expression wrinkles, and where the wrinkles and fine lines lie radially around the mouth and/or the eyes and/or horizontally on the forehead and/or are located in the space between the eyebrows.

All references, patents, applications, tests, standards, documents, publications, brochures, texts, articles, etc. mentioned herein are incorporated herein by reference. Where a numerical limit or range is stated, all values and subranges therewithin are specifically included as if explicitly written out.

What is claimed is:

1. A method for smoothing out wrinkles or fine lines on at least one area of the face or the forehead, comprising applying a skin relaxing effective amount of a substance selected from the group consisting of a sapogenin, a natural extract comprising a sapogenin, a sapogenin ester, and mixtures thereof, wherein the substance(s) can be obtained from a member of the *Dioscorea*, Agave or Liliacea plant families, to at least one area of the face or the forehead marked by at least one of a wrinkle and a fine line.

2. The method of claim 1, wherein said substance is applied to an individual with expression wrinkles and fine lines.

3. The method according to claim 1, wherein said substance is a sapogenin selected from the group consisting of diosgenin, hecogenin, smilagenin, sarsapogenin, tigogenin, yamogenin, yuccagenin, and mixtures thereof.

4. The method according to claim 3, wherein the sapogenin is diosgenin.

5. The method according to claim 1, wherein said substance is a natural extract selected from the group of extracts of rhizomes of *Dioscorea composita, Dioscorea deltoides, Dioscorea floribunda, Dioscorea sylvatica, Dioscorea spiculiflora, Dioscorea opposita, Dioscorea mexicana* and *Dioscorea villosa*.

6. The method according to claim 1, wherein said substance is hecogenin acetate.

7. The method according to claim 1, wherein said substance is present in a composition suitable for the topical application to skin, wherein said substance is present in an amount of 0.1% to 1.5% of the total weight of the composition, and wherein said composition further comprises a physiologically acceptable medium.

8. The method according to claim 7, wherein said composition further comprises at least one compound selected from the group consisting of desquamating agents; moisturizers; depigmenting or propigmenting agents; antiglycation agents; NO-synthase inhibitors; agents for stimulating the synthesis of dermal or epidermal macromolecules and/or for preventing their degradation; agents for stimulating the proliferation of fibroblasts and/or keratinocytes or for stimulating the differentiation of keratinocytes; muscle relaxants; tensioning agents; antipollution agents and/or free-radical scavengers; agents acting on the capillary circulation; agents acting on the energy metabolism of cells; and mixtures thereof.

9. The method of claim 1, wherein the area of the face or the forehead is marked by an expression wrinkle.

10. The method according to claim 1, wherein said at least one of wrinkle and a fine line lie radially around the mouth and/or the eyes and/or horizontally on the forehead and/or are located in the space between the eyebrows.

11. The method according to claim 1, wherein the substance is applied to the skin around the eyes.

12. The method according to claim 1, wherein the substance is applied to the face.

13. The method according to claim 1, wherein the substance is applied to the forehead.

14. The method according to claim 1, wherein the substance is a wild yam extract.

15. The method according to claim 7, wherein said composition is in the form of an emulsion.

16. The method according to claim 7, wherein said composition is in the form of a serum.

17. The method according to claim 1, wherein the substance is from the *Dioscorea* plant family.

18. The method according to claim 1, wherein the substance is from the Agave plant family.

19. The method according to claim 1, wherein the substance is from the Liliacea plant family.

* * * * *